(12) United States Patent
Castor (10) Patent No.: US 7,708,915 B2
(45) Date of Patent: May 4, 2010

(54) POLYMER MICROSPHERES/NANOSPHERES AND ENCAPSULATING THERAPEUTIC PROTEINS THEREIN

(76) Inventor: Trevor P. Castor, 469 Mystic St., Arlington, MA (US) 02174

( * ) Notice: Subject to any disclaimer, the term of this patent is extended or adjusted under 35 U.S.C. 154(b) by 844 days.

(21) Appl. No.: 11/581,021

(22) Filed: Oct. 13, 2006

(65) Prior Publication Data

US 2010/0074961 A1 Mar. 25, 2010

Related U.S. Application Data

(63) Continuation-in-part of application No. 10/840,308, filed on May 6, 2004, now Pat. No. 7,147,806.

(51) Int. Cl.
*B29B 9/00* (2006.01)
(52) U.S. Cl. .......................................................... 264/5
(58) Field of Classification Search ........................ None
See application file for complete search history.

(56) References Cited

U.S. PATENT DOCUMENTS

| 4,582,731 | A | 4/1986 | Smith ........................ 427/421 |
| 4,734,451 | A | 3/1988 | Smith ........................ 524/493 |
| 5,043,280 | A | 8/1991 | Fischer et al. ............. 435/235.1 |
| 5,554,382 | A | 9/1996 | Castor ........................ 424/450 |
| 5,766,637 | A | 6/1998 | Shine et al. ................. 424/497 |
| 6,124,226 | A | 9/2000 | Nielsen et al. ................. 502/9 |
| 6,562,605 | B1* | 5/2003 | Beckman et al. ............ 435/183 |
| 7,208,106 | B2* | 4/2007 | Shekunov et al. ............. 264/5 |
| 2005/0082701 | A1* | 4/2005 | Shekunov et al. ............. 264/5 |

OTHER PUBLICATIONS

Langer, R., Cima, L.G., Tamada, J.A. and Wintermantel, E. "Future Directions in Biomaterials", *Biomaterials*, 11:738-45 (1990).
Mathiowitz, E., Jacob, J.S., Jong, Y.S., Carino, G.P., Chickering, D.E., Chaturvadi, P., Santos, C.A., Vijaaraghavan, K., Montgomery, S., Bassett, M. and Morrell, C. "Biologically Erodable Microspheres as Potential Oral Drug Delivery Systems", *Nature*, 386:410-4 (1997).

* cited by examiner

*Primary Examiner*—Mary Lynn F Theisen
(74) *Attorney, Agent, or Firm*—Burns & Levinson, LLP; Janine M. Susan (57) ABSTRACT

This invention is an improved process to formulate polymeric microspheres/nanospheres and encapsulate therapeutic proteins or other useful substances, and a polymer sphere apparatus. The invention is also methods of purifying protein-containing-polymeric-microspheres from unused polymer, and an apparatus therefore.

6 Claims, 7 Drawing Sheets

POLYMER MICROSPHERES/NANOSPHERES AND ENCAPSULATING THERAPEUTIC PROTEINS THEREIN

RELATED APPLICATIONS

This application is a continuation-in-part of U.S. application Ser. No. 10/840,308, filed May 6, 2004, now U.S. Pat. No. 7,147,806 which in turn claims priority to and the benefit of U.S. application Ser. No. 09/750,473, filed Dec. 29, 2000; the entire contents of each is incorporated herein by reference.

BACKGROUND OF THE INVENTION

Conventional methods of drug delivery such as tablets or injections provide an initial spike of therapeutic agent in a subject's system followed by a period of decay. Dosage is frequently limited by adverse side effects engendered by the elevated, albeit temporary, high level of agent. Furthermore, as the agent is cleared from the body, its concentration will most likely fall below a useful level prior to the next treatment. For many drugs, the ideal is a steady level over a prolonged period ranging from hours to years. This type of profile can be attained with the use of controlled release technology. Improved techniques for controlled release of therapeutic agents is an area of great importance to the medical field, the pharmaceutical industry, and the public that they serve.

One of the most promising methods for controlled release involves the use of degradable or erodable polymers. Following administration via ingestion or injection, the polymer is slowly eroded by body fluids to yield biocompatible breakdown products. Concurrently, drug is released from a polymeric particle by diffusion through the polymer matrix as well as by surface erosion.

Supercritical fluids offer considerable promise as vehicles for the formation of polymeric particles of biomedical interest. Two techniques have been reported to date to formulate poly(L-lactic acid) (PLA) microparticles. In the first method, PLA is dissolved in the supercritical fluid, and particles are formed as a result of rapid expansion of the supercritical fluid. This process is known as rapid expansion of supercritical solution (RESS). RESS is a clear alternative to the conventional methods for the production of drug-loaded polymeric microparticles since it requires no surfactants, yields a solvent-free product, and allows rapid processing at moderate conditions. Therapeutics must be soluble in the supercritical fluid system used; however, most therapeutic proteins are not directly soluble in supercritical fluid systems.

In a second method, PLA is solubilized in the organic solvent and sprayed into the supercritical fluid continuous phase. Here supercritical fluid is used as an anti-solvent that causes particle precipitation from the liquid. This method is known as gas anti-solvent precipitation (GAS). The advantage of GAS over RESS is that the therapeutic agent does not have to be soluble in the supercritical fluid, but only in a suitable organic solvent. The solubility of most proteins in organic solvents is negligible, necessitating the use of large volumes of organic solvents. The disadvantage is that organic solvent must be utilized, although the amount of organic solvent used may be considerably less than with conventional processes. Organic solvents can cause significant deterioration to the bioactivity of protein therapeutics.

In addition to reduction or elimination of organic solvent usage, use of supercritical fluids for the production of polymer microspheres and nanospheres can impart advantages of product sterility.

At present, large-scale production of polymeric microspheres utilize many processing steps and require large quantities of organic solvents. The process is very time consuming, costly and inefficient. Generally, such polymeric microspheres have a wide dispersion of particle size. Such polymeric spheres tend to have a median size greater than 100 microns in diameter. In addition, the exposure of therapeutic agent to the organic solvent may adversely affect the integrity of the final product. The organic solvent must be removed and the product may become contaminated with residual organic solvent that may be toxic. The process steps may also compromise sterility, or do not provide sterility.

Hydrophilic polymer microspheres containing proteins can be formed by a process that utilizes a large excess of polyethylene glycol (PEG). The PEG can be removed with organic solvents such as methylene chloride or ethyl acetate. Such removal utilizes large quantities of organic solvent that could damage protein integrity. There are also problems of trace residual organics that could be harmful to patients and are not acceptable by the regulatory authorities, and the environmental consequence of disposing of large quantities of toxic organic solvents.

SUMMARY OF THE INVENTION

The present invention is related to methods of purifying protein-containing-polymer-microspheres. The integrity of proteins encapsulated in polymer microspheres as well as the microspheres can be conserved after selective extraction/removal of PEG by SuperFluids™, which are supercritical, near-critical or critical fluid solvents with or without polar cosolvents. The invention provides SuperFluids™ conditions that efficiently solubilize PEG, do not damage the encapsulated proteins, and do not disrupt the structure of the polymer microspheres containing the proteins, and the design and use of an apparatus to perform the aforementioned.

The present invention is related to polymeric spheres and methods of using supercritical fluids for making uniform polymer spheres. The uniformity and integrity of such spheres make such spheres ideal for containing therapeutic agents such as biological molecules. The methods require reduced processing time and preparation costs.

In one embodiment of the present invention, a method of making polymeric spheres comprising the steps of providing a polymer solution of a polymeric material dissolved in a first fluid is disclosed. In one aspect, the first fluid comprises a supercritical, critical or near-critical fluid. Next, the polymer solution is depressurized as the polymer solution exits one or more orifices of an apparatus in the presence of a low solubility fluid. The low solubility fluid has low volatility and the polymeric material is in a concentration which exceeds the solubility of the polymeric material in the low solubility fluid. The polymeric material forms spheres and the first fluid is removed during depressurization.

In another embodiment, a method for incorporating bioactive materials in polymeric spheres is disclosed. A polymeric material is contacted with a first fluid. This first fluid comprises a critical, supercritical, or near critical fluid with or without one or more cosolvents. This first admixture of polymeric material and first fluid are admixed with a second fluid forming a second admixture, wherein the second fluid comprises a bioactive or therapeutic agent. This second fluid can comprise a critical, supercritical, or near critical fluid together with a cosolvent such as an alcohol, an aqueous solvent such as distilled water or mixtures thereof. The second admixture is subjected to depressurization. This depressurization can be accomplished by releasing the second admixture through an orifice of the apparatus into a medium at, for example, atmospheric pressure. In one aspect, the medium into which the second admixture is released is a third fluid. This third fluid is a low solubility solvent.

Figure 1:
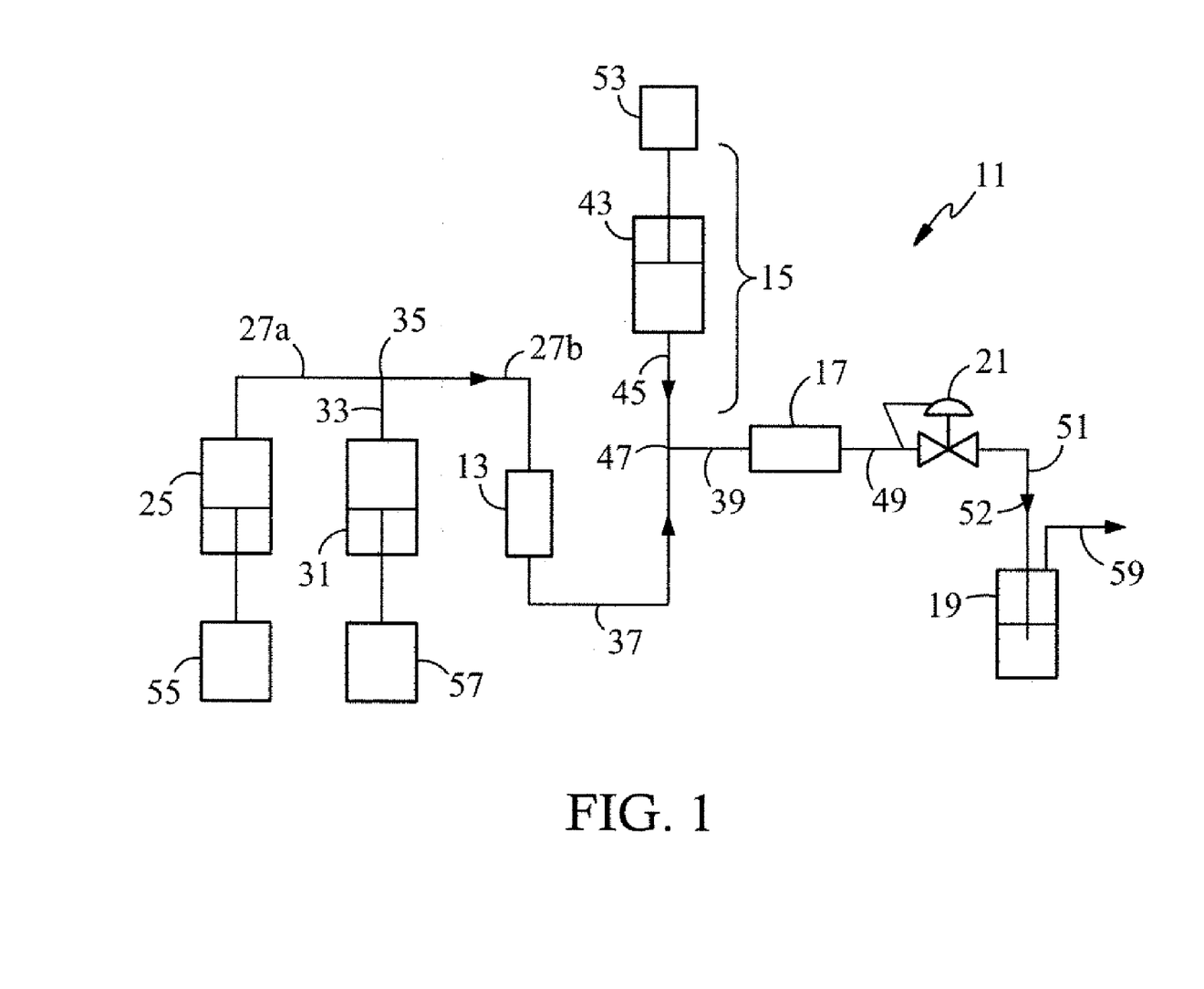
FIG. 1 is a schematic diagram of a Superfluids™ Polymer MicroSphere/Nanosphere Encapsulation Apparatus according to the invention.
Figure 4:
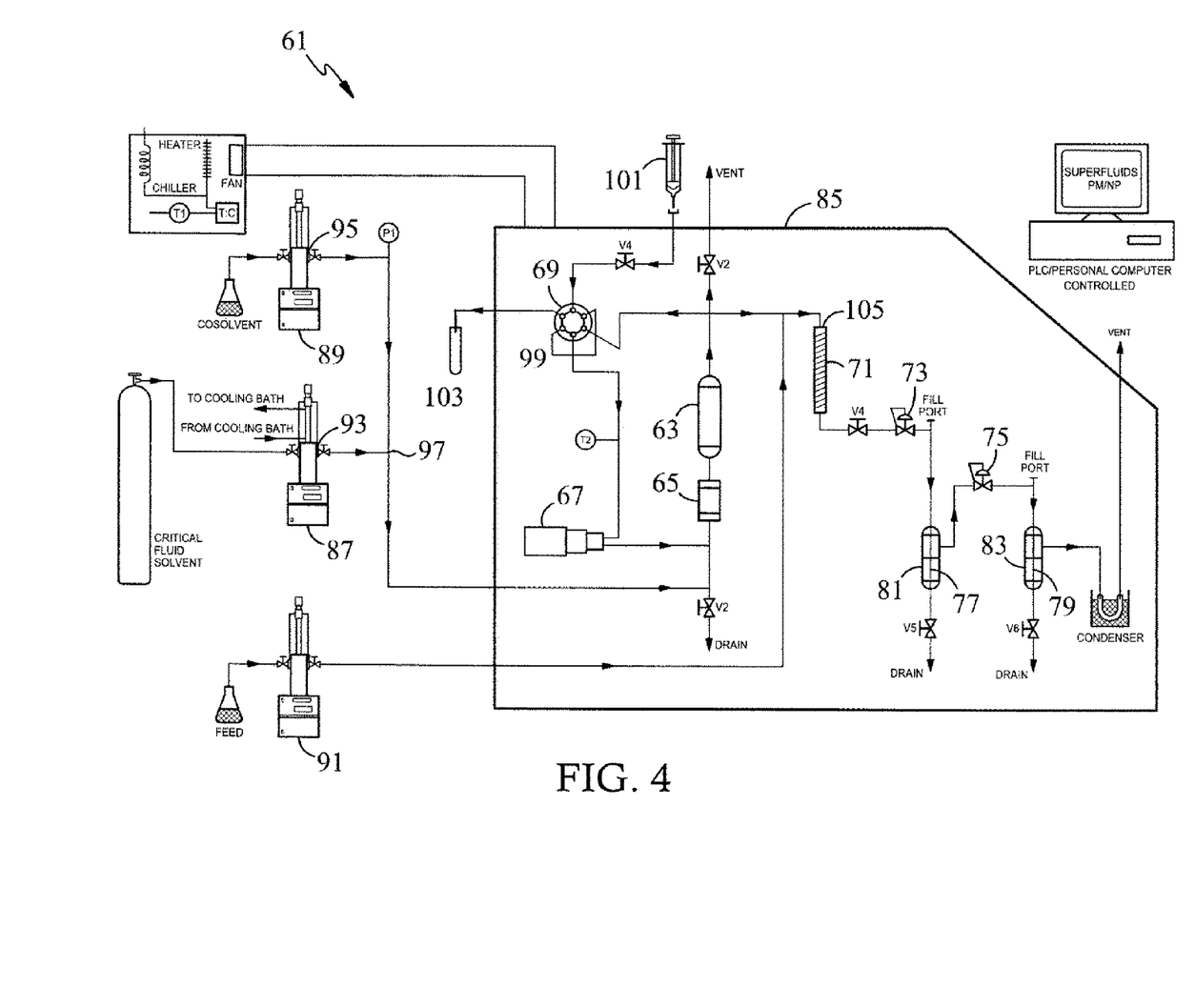
FIG. 4 is a process flow diagram of a SuperFluids™ Polymer Micro/Nanoencapsulation Apparatus according to the invention.

A further embodiment of the present invention features an apparatus for forming one or more polymeric spheres as shown in FIGS. 1 and 4. The apparatus comprises an admixture vessel, a depressurization chamber and an orifice. The admixture vessel is for receiving and containing a polymer solution of a polymeric material in a first fluid, the first fluid consisting of a supercritical, critical or near-critical fluid. The depressurization chamber contains a low solubility fluid and is in fluid communication with the admixture vessel by the orifice. The depressurization chamber receives the polymer solution as said polymer solution exits the orifices in the presence of a low solubility fluid. The low solubility fluid has low volatility and the polymeric material is in a concentration which exceeds its solubility in such fluid. The polymeric material forms spheres and the first fluid is removed during depressurization.

An alternative embodiment of the present invention is a method of solubilizing polymers, such as polyethylene glycol (PEG), in a supercritical or near-critical fluid. Polymer is loaded into a sample vessel, a first pump is charged or primed with a supercritical or near-critical fluid and a second pump is charged or primed with a cosolvent. The pumps are subjected to pressure and used to mix the supercritical or near-critical fluid with the cosolvent. Polymer is added to the fluid-cosolvent mixture and it is solubilized in the mixture and collected.

Examples of supercritical or near-critical fluids include carbon dioxide, propane, fluorinated propane, Freon-23 or Freon 22. Other critical fluid solvents are listed in Table 1. The cosolvent is chosen to modify the polarity of the supercritical or near-critical fluid. Examples of cosolvents include ethanol and methanol. The ratio of supercritical or near-critical fluid to cosolvent can be varied and the solvation properties of polymer in the mixture will depend on the pressure and temperature of the system. One example is a fluid-cosolvent mixture of carbon dioxide:ethanol::70:30 with an operating pressure of about 2500 psig-5000 psig and temperature of about 20° C.-40° C.

A further embodiment of the present invention is a method of purifying protein-containing-polymer-microspheres by removing or extracting unused polymer. A protein-containing-polymer-microspheres product is loaded into an extractor and the extractor is pressurized with a supercritical or near-critical fluid. A first pump is charged or primed with a supercritical or near-critical fluid, a second pump is charged or primed with a cosolvent and the pumps are pressurized. The supercritical or near-critical fluid and cosolvent are mixed under pressure and the fluid-cosolvent mixture is passed through the extractor. Unused polymer is solubilized in the mixture and flows out of the extractor to be collected in cosolvent. Then the extractor is decompressed from both ends simultaneously and purified protein-containing-polymer-microspheres can be recovered.

Examples of supercritical or near-critical fluids include carbon dioxide, propane, fluorinated propane, Freon-23 or Freon 22. Other critical fluid solvents are listed in Table 1. The cosolvent is chosen to modify the polarity of the supercritical or near-critical fluid. Examples of cosolvents include ethanol and methanol. The ratio of supercritical or near-critical fluid to cosolvent can be varied and the solvation properties of polymer in the mixture will depend on the pressure and temperature of the system. One example is a fluid-cosolvent mixture of carbon dioxide:ethanol::70:30 with an operating pressure of about 2500 psig-5000 psig and temperature of about 10° C.-40° C.

Figure 5:
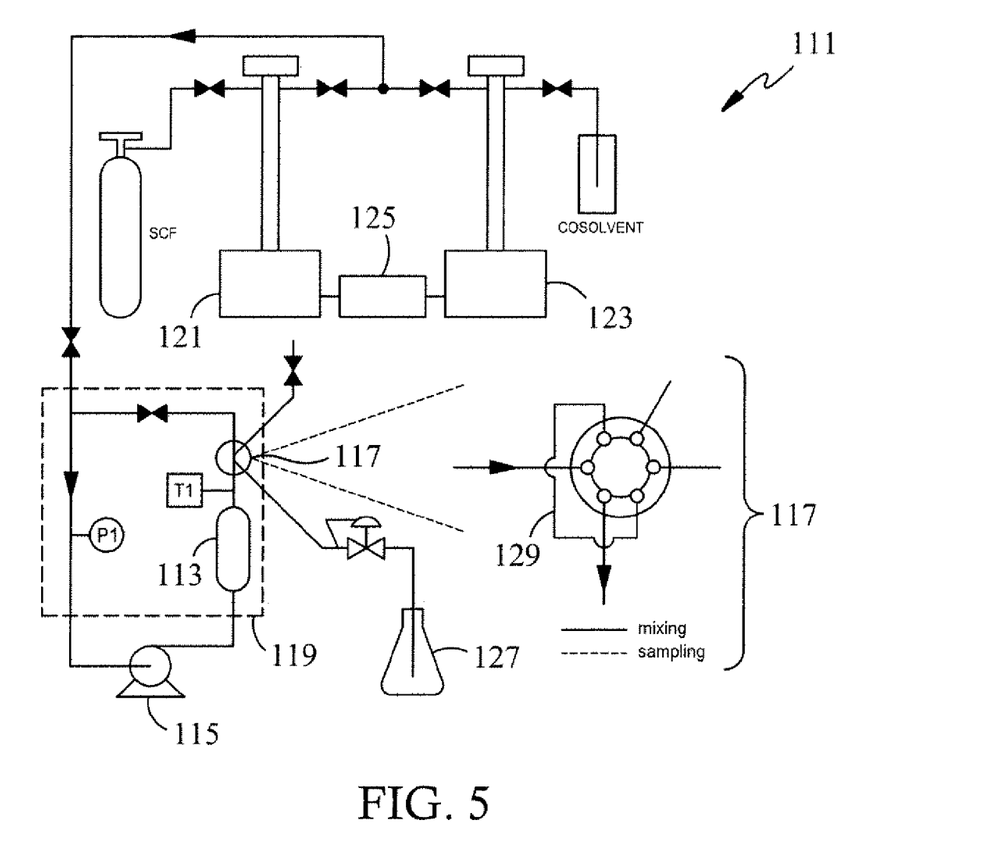
FIG. 5 is a schematic diagram of an apparatus for measuring the solubility of polymers and other chemical entities in SuperFluids™ at different pressures and temperatures.
Figure 6:
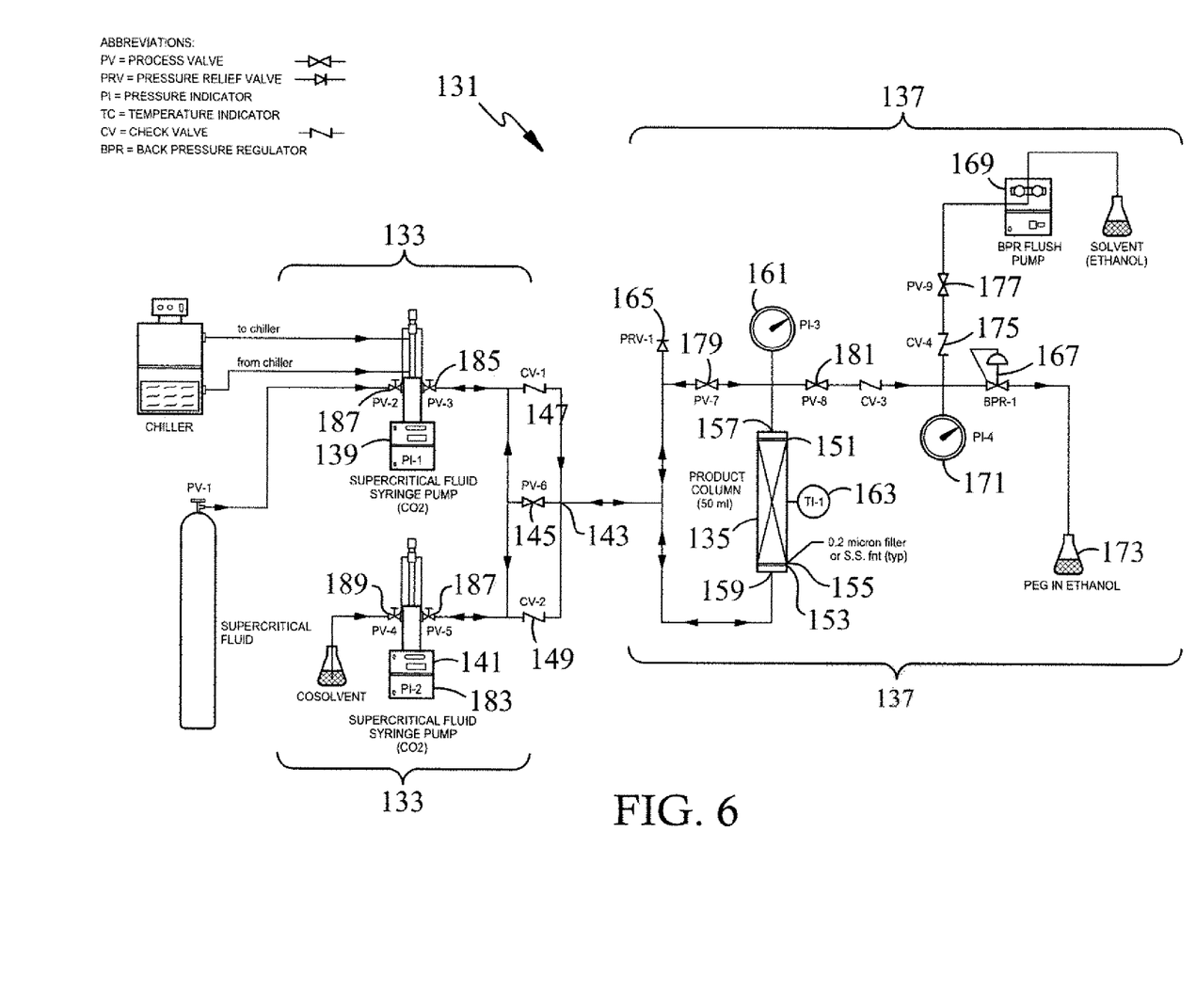
FIG. 6 is a process flow diagram of an apparatus for utilizing SuperFluids™ to extract/remove polyethylene glycol (PEG) from hydrophilic polymer microspheres containing proteins with high retention of protein and microspheres integrity.

A further embodiment of the invention is an apparatus for purifying protein-containing-polymer-microspheres as shown in FIGS. 5 and 6. The main components include a dual syringe pumping system, an extractor and a recovery system. The extractor can be a high-pressure column containing filters or frits at each end. Alternatively, the extractor can include an insert for collecting or containing the purified microspheres.

DETAILED DESCRIPTION OF THE INVENTION

The present invention is related to polymeric spheres and methods of using supercritical fluids for making uniform polymer spheres. The uniformity and integrity of such spheres make such spheres ideal for containing therapeutic agents such as biological molecules and pharmaceuticals. The methods require reduced processing time and preparation costs.

Aspects of the present invention employ materials known as supercritical, critical or near-critical fluids. A material becomes a critical fluid at conditions which equal its critical temperature and critical pressure. A material becomes a supercritical fluid at conditions which equal or exceed both its critical temperature and critical pressure. The parameters of critical temperature and critical pressure are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power. At a pressure of 3,000 psig (204 atm) and a temperature of 40° C., carbon dioxide has a density of approximately 0.8 g/cc and behaves much like a nonpolar organic solvent, having a dipole moment of zero debyes.

A supercritical fluid displays a wide spectrum of solvation power as its density is strongly dependent upon temperature and pressure. Temperature changes of tens of degrees or pressure changes by tens of atmospheres can change a compound's solubility in a supercritical fluid by an order of magnitude or more. This feature allows for the fine-tuning of solvation power and the fractionation of mixed solutes. The selectivity of nonpolar supercritical fluid solvents can also be enhanced by addition of compounds known as modifiers (also referred to as entrainers or cosolvents). These modifiers are typically somewhat polar organic solvents such as acetone, ethanol, methanol, methylene chloride or ethyl acetate. Varying the proportion of modifier allows a wide latitude in the variation of solvent power.

In addition to their unique solubilization characteristics, supercritical fluids possess other physicochemical properties which add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

A material at conditions that border its supercritical state will have properties that are similar to those of the substance in the supercritical state. These so-called "near-critical" fluids are also useful for the practice of this invention. For the purposes of this invention, a near-critical fluid is defined as a fluid which is (a) at a temperature between its critical temperature ($T_c$) and 75% of its critical temperature and at a pressure at least 75% of its critical pressure, or (b) at a pressure between its critical pressure ($P_c$) and 75% of its critical pressure and at a temperature at least 75% of its critical temperature. In this definition, pressure and temperature are defined on absolute scales, e.g., Kelvin and psia. Table 1 shows how these requirements relate to some of the fluids relevant to this invention. To simplify the terminology, materials which are utilized under conditions which are supercritical, near-critical, or exactly at their critical point will jointly be referred to as "SCCNC" fluids. The term Superfluids™, as used herein, refers to SCCNC fluids with or without cosolvents.

TABLE 1

Physical Properties of Critical Fluid Solvents

| Fluid | Formula | BP (° C.) | $P_{vap}$ (psia @ 25° C.) | $T_c$ (° C.) | $P_c$ (psia) | 0.75 $T_c$ (° C.) | 0.75 $P_c$ (psia) |
|---|---|---|---|---|---|---|---|
| Carbon dioxide | $CO_2$ | −78.5 | 860 | 31.1 | 1070 | −45.0 | 803 |
| Nitrous oxide | $N_2O$ | −88.5 | 700 | 36.5 | 1051 | −41.0 | 788 |
| Propane | $C_3H_8$ | −42.1 | 130 | 96.7 | 616 | 4.2 | 462 |
| Ethane | $C_2H_6$ | −88.7 | 570 | 32.3 | 709 | −44.1 | 531 |
| Ethylene | $C_2H_4$ | −103.8 | NA | 9.3 | 731 | −61.4 | 548 |
| Freon 11 | $CCl_3F$ | 23.8 | 15 | 198.1 | 639 | 80.3 | 480 |
| Freon 21 | $CHCl_2F$ | 8.9 | 24 | 178.5 | 750 | 65.6 | 562 |
| Freon 22 | $CHClF_2$ | −40.8 | 140 | 96.1 | 722 | 3.8 | 541 |
| Freon 23 | $CHF_3$ | −82.2 | 630 | 26.1 | 700 | −48.7 | 525 |

Table 1 Notes:
BP = Normal boiling point; $P_{vap}$ = Vapor pressure; $T_c$ = critical temperature; $P_c$ = critical pressure A viable method for controlled release involves the use of degradable or erodable polymers. These are typically formulated as microparticles or microspheres with a size ranging from a maximum of 50 μM down to approximately 0.1 μm. Following administration via ingestion or injection, the polymer is slowly eroded by body fluids to yield biocompatible breakdown products. Concurrently, drug is released from the particle by diffusion through the polymer matrix as well as by surface erosion.

A commonly used bioerodable polymer is of the poly(hydroxyacid) type, in particular poly(L-lactic acid), poly(D,L-lactic acid), poly(glycolic acid), and copolymers thereof. A typical copolymer used for microsphere/microparticle formation is poly(lactide-co-glycolide), abbreviated as PLGA. These materials are broken down in the body to the non-toxic products lactic acid and glycolic acid, and have been approved by the Food and Drug Administration for use as resorbable sutures, in bone implants, and as controlled release microspheres. Other polymers being utilized include poly (fumaric anhydride) and poly(sebacic anhydride). Mathiowitz, E., Jacob, J. S., Jong, Y. S., Carino, G. P., Chickering, D. E., Chaturvedi, P., Santos, C. A., Vijayaraghavan, K., Montgomery, S., Bassett, M. and Morrell, C., Biologically Erodable Microspheres as Potential Oral Drug Delivery Systems, *Nature*, 386:410-414, 1997. Another polymer that can be used for microsphere/microparticle formation is polyethylene glycol, abbreviated PEG. The use of polymeric microspheres for controlled drug delivery has been the subject of a number of reviews. Langer, R., Cima, L. G., Tamada, J. A. and Wintermantel, E.: "Future Directions in Biomaterials," *Biomaterials*, 11:738-745, 1990, the entire teachings of which are incorporated herein by reference.

A typical copolymer used for microsphere/microparticle formation is poly(lactide-co-glycolide), abbreviated as PLGA. Conventional drug-containing PLGA microspheres are prepared by a solvent evaporation method using a double emulsion technique which involves four major sequential steps: (1) mixing of PLGA (in methylene chloride) with drug (in water) followed by sonication to obtain a water-in-oil (W/O) emulsion; (2) mixing of W/O with a second aqueous PVA solution followed by sonication to obtain (water-in-oil)-in-water emulsion; (3) solvent evaporation causing microspheres to harden; and (4) collection of microspheres by centrifugation followed by three washing steps.

In an alternative process, a five step process is employed: (1) protein particles are first milled into a fine powder in the 1 μm to 10 μm range; (2) a suspension of the protein particles is made in a solution of PLGA in methylene chloride, ethyl acetate or DMSO; (3) the organic solvent/PLGA/protein mixture is injected into liquid nitrogen to form frozen microspheres; (4) the frozen microspheres are transferred into ethanol at −100° C. to back-extract the organic solvent three times; and (5) the microspheres are filtered, lyophilized and packaged.

In one embodiment of the present invention, a method of making polymeric spheres comprising the steps of providing a polymer solution of a polymeric material dissolved in a first fluid is disclosed. The apparatus used is depicted in FIGS. 1 and 4. In one aspect, the first fluid comprises a supercritical, critical or near-critical fluid. Next, the polymer solution is depressurized as the polymer solution exits one or more orifices of the apparatus in the presence of a low solubility fluid. The low solubility fluid has low volatility and the polymeric material is in a concentration which exceeds the solubility of the polymeric material in the low solubility fluid. The polymeric material forms spheres and the first fluid is removed during depressurization.

The polymeric spheres of the present invention have an average diameter of between 0.01 and 10.0 microns and, in one aspect, between 0.1 and 1.0 microns. The narrow range of diameter of the microspheres and nanospheres that can be attained with the present method is unusual and surprising.

In one aspect, the polymeric material is selected from one or more of the group of polymers consisting of poly(L-lactic acid), poly(D, L-lactic acid), poly(glycolic acid) and carboxylic acid and ester derivatives thereof, poly(fumaric anhydride) and poly(sebacic anhydride) and polyethylene glycol.

In one aspect, the first fluid can comprise carbon dioxide, nitrous oxide, ethylene, ethane, propane and fluorohydrocarbons. The first fluid can also contain modifiers. Examples of such modifiers include, but are not limited to, methanol, ethanol, propanol, butanol, methylene chloride, ethyl acetate and acetone.

In one aspect, the temperature and pressure for a SCCNC comprising carbon dioxide are a temperature in the range of about 10 to about 60° C. and a pressure in the range of about 1,000 to about 5,000 psig.

The present invention also relates to methods used to incorporate bioactive materials in polymeric spheres.

In one embodiment, a polymeric material is contacted with a first fluid. This first fluid comprises a critical, supercritical, or near critical fluid with or without one or more cosolvents. This first admixture of polymeric material and first fluid are admixed with a second fluid forming a second admixture, wherein the second fluid comprises a bioactive or therapeutic agent (such as a pharmaceutical, peptide, protein, nucleic acid, and other biological molecules well known to those skilled in the art). (As used herein, the term "bioactive" refers to compositions which cause a change or modification of a living organism in the nature of pharmaceuticals, drugs, toxins, biocides and the like.) This second fluid can comprise a critical, supercritical, or near critical fluid together with a cosolvent such as an alcohol, an aqueous solvent such as distilled water or mixtures thereof. The second admixture is subjected to depressurization. This depressurization can be accomplished by releasing the second admixture through an orifice of the apparatus into a medium at or near, for example, atmospheric pressure. In one aspect, the medium into which the second admixture is released is a third fluid. This third fluid is a low solubility solvent. During depressurization, high volatility solvents such as a critical, supercritical, or near critical fluid are removed from low volatility solvents such as water containing polymeric spheres. Sterile filtration and solvent evaporation can then be used to harvest the polymeric spheres.

In one aspect, the bioactive agent is dissolved in the first fluid or dissolved in, or is held as a suspension or as an emulsion in the second fluid which is combined with the first fluid and polymeric material. In a particular aspect, the fluid used to dissolve or hold the bioactive material is a supercritical, critical or near-critical fluid.

In one aspect, the third fluid (or low solubility fluid) is selected from the group of solvents consisting of water, PVA, PBS, and liquid nitrogen, with or without a cosolvent, such as an alcohol, an aqueous solvent such as distilled water or mixtures of the aforementioned. The third fluid can also contain a chemical agent for stabilizing the polymeric spheres by cross-linkage or other means well known to those skilled in the art. The low solubility fluid can also be comprised of a critical, supercritical or near-critical fluid or mixtures of the aforementioned.

One method of the present invention for making polymeric spheres having an average diameter of between about 0.01 to about 10 microns and a bioactive material comprises the steps of providing a polymer solution of a polymeric material in a first fluid, the first fluid consisting of a supercritical, critical or near-critical fluid. Next, the method comprises the step of providing a bioactive fluid having bioactive material. Next, an admixture of the first solution and the bioactive fluid is formed, to form an admixture solution, the admixture solution comprising a supercritical, critical or near-critical fluid. The admixture solution is depressurized as the admixture solution exits one or more orifices in the presence of a low solubility fluid. The low solubility fluid has low volatility and the polymeric material is in a concentration which exceeds its solubility in this fluid. The polymeric material forms spheres having an average diameter of 0.1 to 1.0 microns which spheres contain the bioactive material as the first fluid is removed during depressurization.

A further embodiment of the present invention features an apparatus 11 for forming one or more polymeric spheres. The apparatus 11 comprises an admixture vessel 17, a depressurization chamber 19 and an orifice nozzle 52. The admixture vessel 17 is for receiving and containing a polymer solution of a polymeric material in a first fluid, the first fluid consisting of a supercritical, critical or near-critical fluid. The depressurization chamber 19 contains a low solubility fluid and is in fluid communication with the admixture vessel 17 by conduits 49 and 51, back pressure regulator 21 and the orifice nozzle 52. The depressurization chamber 19 receives the polymer solution as said polymer solution exits the orifice nozzle 52 in the presence of a low solubility fluid. The low solubility fluid has low volatility and the polymeric material is in a concentration which exceeds its solubility in such fluid. The polymeric material forms spheres and the first fluid is removed during depressurization.

The apparatus 11 is used to make spheres having an average diameter of 0.01 to 10.0 microns.

In one aspect, the admixture vessel 17 receives a bioactive material. The bioactive material is dissolved in a solvent or held as a suspension in a fluid or held in an emulsion. Such bioactive material is incorporated into the spheres during depressurization.

In one aspect, the apparatus 11 further comprises a polymer vessel 13 for forming a solution of a polymer in a supercritical, critical or near-critical fluid. The polymer vessel 13 is in fluid communication with the admixture vessel 17.

In one aspect, the apparatus 11 further comprises a bioactive material vessel 53 for forming a suspension, solution or emulsion of said bioactive material in a fluid. The bioactive vessel 53 is in communication with the admixture vessel 17.

Sterile filtration and solvent evaporation can then be used to harvest the polymeric spheres. SCCNC fluids also sterilize the materials in which such fluids are incorporated upon rapid depressurization, such as depressurization through an orifice.

The use of SCCNC fluids allows for easy removal of much of the solvent by mere depressurization. Use of a single apparatus to perform polymer sphere formation and encapsulate therapeutic agents minimizes labor and increases efficiency. Indeed, the entire process can be readily automated. The use of SCCNC fluids allows process conditions to be readily varied by temperature, pressure, or modifier solvents, minimizing equipment needs, processing time, potential for contamination, and loss of yield. The use of SCCNC fluids eliminates the need for toxic organic solvents such as in methylene chloride, ethyl acetate or DMSO and eliminates the presence of these toxic organic solvents in the final product.

The present apparatus is described with respect to FIG. 1 which depicts in schematic form a polymer sphere apparatus 11. The polymer sphere apparatus 11 is comprised of the following major elements: a polymer vessel 13, a bioactive 
injection assembly 15, an admixture chamber 17, a depressurization vessel 19, a back pressure regulator 21 and an orifice nozzle 52.

Polymer vessel 13 is in fluid communication with a SCCNC syringe pump 25 via conduits 27a and 27b. SCNCC pump 25 is in fluid communication with a source of SCCNC fluid 55.

Polymer vessel 13 is also in fluid communication with a modifier syringe pump 31 via conduit 33 which intersects with conduits 27a and 27b at junction 35. Modifier syringe pump 31 is in communication with a source of modifiers 57.

Polymer vessel 13 is loaded with polymer. And, polymer vessel 13 receives SCNCC fluid from SCNCC pump 25 via conduits 27a and 27b. Polymer vessel 13 receives modifiers from Modifier pump 31 via conduit 33. Polymer is dissolved in the SCNCC fluid and modifier to form a polymer solution.

Polymer vessel 13 is in fluid communication with admixture chamber 17 via conduits 37 and 39. Admixture chamber 17 is also in fluid communication with bioactive injection assembly 15. Bioactive injection assembly 15 comprises bioactive syringe pump 43, a source of bioactive material 53 and conduit 45. Bioactive syringe pump 43 is in communication with a source of bioactive material and pressurizes and compels such material through conduit 45. Conduit 45 is in communication with admixture chamber 17 via conduit 39 which intersects conduit 45 at junction 47. Preferably junction 47 is a mixing "T".

Admixture vessel 17 is in the nature of an inline mixer and thoroughly mixes incoming streams from the polymer vessel 13 and bioactive injection assembly 15. Admixture vessel 17 is in communication with back pressure regulator 21 via conduit 49. Orifice nozzle 52 is connected to a nozzle defining one or more orifices which discharge into depressurization vessel 19 via conduit 51. Preferably back pressure regulator 21 controls pressure and decompression rates. The size of the orifice nozzle 52 determines the microsphere/nanosphere diameter.

The operating pressure of the system can be preset at a precise level via a computerized controller (not shown) that is part of the syringe pumps 25, 31, and 43. Temperature control in the system is achieved by enclosing the apparatus 11 in ¼" Lexan sheet while utilizing a Neslab heating/cooling system coupled with a heat exchanger (not shown) to maintain uniform temperature throughout the system.

In a typical experimental run, polymeric materials were first packed into the polymer vessel 13. SCCNC and an ethanolic solution of insulin were charged into the SCNCC syringe pumps 25 and 31, respectively, and brought to the desired operating pressure. In the alternative, an ethanol solution of insulin is charged into bioactive syringe pump 43.

The system was then pressurized with the SCCNC via SCNCC syringe pump 25 to the pressure level equal to that set in modifier syringe pump 31 and bioactive syringe pump 43, and maintained at this level with the back pressure regulator 21. The dynamic operating mode for all pumps were set so that each pump can be operated at its own desired flow rate. The SCCNC stream flowed through the polymer vessel 13, dissolved polymer and contacted the insulin stream at junction 47. The mixture of SCCNC, insulin and polymeric materials was then passed through admixture chamber 17 for further mixing. Finally, the mixed solution entered back pressure regulator 21 and was injected into a 0.1% PVA aqueous solution in the depressurization vessel 19. As a result of supercritical fluid decompression, polymeric spheres containing insulin are formed in the PVA aqueous solution and the expanded supercritical fluid exited the system via a vent line 59 on the depressurization vessel 19.

With respect to purifying protein-containing-polymer-microspheres, SuperFluids™ carbon dioxide and ethanol are both generally regarded as safe (GRAS) and are good candidates for removal of unused polymer, such as PEG and organic solvents. Since PEG is of intermediate polarity, a modifier such as ethanol or methanol is required to modulate the polarity of carbon dioxide that, by itself, is quite nonpolar having a polarity of 0.0 Debyes. Ethanol is preferred to methanol, since it is less toxic and more GRAS. In the presence of water, carbon dioxide can readily form carbonic acid that can cause protein hydrolysis and denaturation. Thus, a key ingredient of this invention is the removal of water from the PEG-polymer microspheres-protein complex before processing with SuperFluids™ carbon dioxide and ethanol. The removal of water is not a requirement if SuperFluids™ such as fluorocarbons and alkanes are utilized to solubilize PEG.

The polymer microspheres could be disrupted by compression during the SuperFluids™ pressurization process and/or by expansion during the decompression process. To maintain the integrity of the polymer microspheres, the PEG-polymer microspheres-protein complex is simultaneously pressurized from both ends of the containing vessel prior to the initiation of the PEG extraction/removal process. After the extraction/removal of PEG is completed, the polymer microspheres-protein complex is slowly decompressed from both ends of the containing vessel by reversing the syringe pumps utilized to pressurize the system.

In various experiments, we have shown that: (1) PEG 3350 can be solvated 14 mg/ml) in a SuperFluids™ carbon dioxide (70%):ethanol (30%) solvent system at 2,500 psig and 20° C.; and (2) protein microspheres can be treated with SuperFluids™ carbon dioxide (70%):ethanol (30%) solvent system at 2,500 psig and 20° C. with (i) high recovery of protein bioactivity after being contacted with the SuperFluids™ solvent, (ii) high recovery of the protein encapsulated in microspheres and (iii) high recovery of intact microspheres under lyophilized conditions in the absence of water and residual ethanol solvent.

Superfluids™ Solubility Apparatus

The solubility experiments were conducted in a SuperFluids™ solubility (SOL) apparatus 111 shown as FIG. 5.

The experimental SuperFluids™ solubility apparatus 111 mainly consists of a sample vessel 113, a circulation pump 115 and a 6-port injection valve 117, all contained in a temperature-controlled chamber 119. An Isco SFX 2-10 supercritical fluid extractor (Isco, Inc., Lincoln, Nebr.) with integral heating/control system is utilized as the sample vessel 113. Two Isco syringe pumps (Isco, Inc., Lincoln, Nebr.), model 260D 121 and 100D 123, are used for supercritical fluid and cosolvent delivery, respectively.

In a typical experiment, PEG 3350 is packed into the sample vessel 113, layer by layer, interspersed with glass wool in order to maximize the contact area between the SuperFluids™ and the candidate material, and minimize mass transfer resistance. The temperature of the system was then adjusted to a setpoint level via an external temperature control unit (not shown in the diagram). Syringe pumps A 121 and B 123 are charged with carbon dioxide and ethanol as cosolvent, respectively, and brought to operating pressure via a computerized controller 125. The controller 125 is used to set the volume ratio of supercritical carbon dioxide and ethanol. The SuperFluids™ mixture is then charged to the system. When the pressure reaches the desired level, the circulation pump 115 is turned on to ensure that the SuperFluids™ and the PEG 3350 are thoroughly mixed. After the desired mixing time is achieved, the injection valve 117 is then switched to the "sampling" position to trap PEG 3350 dissolved in the SuperFluids™ stream. The SuperFluids™ and PEG 3350 in the sample loop 129 are then discharged into a sample collection vessel 127. A suitable solvent is then used to flush the PEG 3350 from the sample loop 129 and nitrogen gas is used to displace all fluids from the sample loop 129. The collected sample is then analyzed to determine the amount of PEG 3350 solubilized in the sample loop 129 of known volume.

Apparatus for Superfluids™ Extraction/Removal of Unused Polymer from Hydrophilic Microspheres Containing Proteins The apparatus 131 for utilizing SuperFluids™ to extract/remove PEG 3350 from hydrophilic polymer microspheres containing proteins with high retention of protein and microspheres integrity is shown by a process flow diagram (PFD) in FIG. 6.

This apparatus 131 consists of three major components: (1) a dual syringe pumping system 133; (2) an extractor 135; and (3) a SuperFluids™ and PEG recovery system 137. This apparatus 131 is designed and constructed to operate up to 5,000 psig and 60° C.

The dual syringe pumping system 133 (rated at 7,500 psig) will consist of two Isco 260D high-pressure syringe pumps 139 and 141 connected by a common controller (not shown). The 260D 139 that is used to pump the near-critical fluid such as carbon dioxide is chilled to minimize vapor lock. The pumps 139 and 141 can be individually or collectively controlled to precisely deliver fluid in a constant volume mode in specific pre-defined ratios. The pumps 139 and 141 can also be precisely controlled to operate in the constant pressure mode. The pumps 139 and 141 are connected so that the supercritical or near-critical fluid and the co-solvent are first contacted at a mixing-tee 143 prior to introduction in the extractor 135. The pumps 139 and 141 are also connected for controlled depressurization through reversing the flow by opening process valve PV-6 145 in order to bypass check valves CV-1 147 and CV-2 149.

The extractor 135, rated at 10,000 psig, is a high-pressure stainless-steel (SS) 50 ml column (10 cm×an ID of 2.54 cm) with bolted end-caps 151 and 153. The extractor 135 is modified to include a 0.2-micron filter 155 and/or SS frit 155 at the top 151 and bottom end-caps 153. The 0.2-micron filters and/or SS frits 155 are designed to retain the protein microspheres in the column 135 after the extraction of the PEG 3350. Alternatively, the PEG protein-microspheres can be placed in an insert within the column; such an insert will facilitate product recovery after extraction is completed.

The extraction column 135 has an inlet 157 and an outlet 159 to allow simultaneous pressurization from the top and the bottom to minimize any potential extrusion of the protein microspheres into the 0.2-micron filters and/or SS frits 155. The column 135 and its connecting lines are fitted with a pressure gauge 161, a temperature indicator 163, and a pressure relief valve 165. If needed, temperature can be controlled and/or readily varied up or down by the addition of heating/chilling coils around the extractor. Indeed reducing the temperature to 10° C., for example, can result in an increase in the retention of protein integrity while reducing operating pressure and maintaining high PEG 3350 solubility in the SuperFluids™ stream.

The SuperFluids™ and polymer recovery system 137 consists of a back-pressure regulator (BPR-1) 167, a BPR high-pressure flush pump 169, a pressure gauge 171, a PEG 3350 collection vessel 173 and associated check 175 and process valves 177. BPR-1 167 may require heating to minimize freezing due to Joule-Thompson cooling effects during depressurization.

During a typical operation, the PEG polymer-microspheres-protein product is loaded into the extractor 135. The loaded column is then connected to the input and output lines and the system pressurized with carbon dioxide ($CO_2$) or alternative supercritical or near-critical solvent with PV-7 179 open, and PV-8 181 and PV-6 145 closed. The supercritical fluid syringe pump 139 is operated in the constant pressure mode closed until the operating pressure, 2,500 psig, is achieved. PV-7 179 will then be closed, PV-8 181 is opened and BPR-1 167 adjusted until there is no flow in the collection vessel 173 and the supercritical fluid syringe pump 139. The pressure is thus maintained at the set point of 2,500 psig if there are no leaks in the system 131. Minor leaks (less than 0.1 ml/min) may be tolerable and are recorded; pressure is maintained by the syringe pump 139.

After stabilization of the system 131, the supercritical fluid syringe pump 139 is changed into the constant flow mode at the pre-set extraction flow rate (e.g., 10 ml/min). The BPR flush pump 169 will then be turned on, PV-9 177 open and flow initiated (e.g., at 1.0 ml/min) to continuously flush BPR-1 167. The system 131 is run for about 10 minutes in this mode. The co-solvent pump 141 is started in the constant pressure mode until system pressure is achieved on PI-2 183, and then step-wise changed to the constant flow-rate mode until the designed co-solvent ratio is achieved (e.g., $CO_2$:ethanol::70:30). The system 131 is run in this mode for the designed extraction time (e.g., 60 minutes assuming a dynamic solubility of 10 mg/ml and a flow-rate of 10 ml/min).

At the end of the extraction step, the co-solvent pump 141 is turned off while flow is continued with the supercritical pump 139 until all co-solvent (ethanol) is removed from the system. The supercritical fluid and the BPR flush pumps 139 and 169 are then be turned off. PV-8 181 and PV-9 177 are closed, and PV-6 145 and PV-7 179 are opened. PV-3 183 and PV-5 185 are also closed, and the supercritical fluid and co-solvent pumps 139 and 141 are respectively emptied into the vent and solvent waste recovery vessels (not shown). After emptying the syringe pumps 139 and 141, PV-2 187 and PV-4 189 are closed and PV-3 185 and PV-5 187 are slowly opened. The syringe pumps 139 and 141 are then run in the reverse (fill) mode at a pre-defined rate designed to minimize disruption of the polymer microspheres. This rate is estimated from theoretical diffusion concepts, but can be based on experimental data.

EXAMPLES

For preliminary experiments, 50:50 mixtures of poly(D,L-lactic glycolic acid) with molecular weights of 3,000, 50,000 and 100,000 (Sigma Chemicals, St. Louis, Mo.) were utilized. For most microsphere and some solubility experiments, Medisorb® biodegradable polymers (Alkermes, Inc., Cincinnati, Ohio) were utilized. The specifications on the Medisorb polymers are listed in Table 2. "A" indicates that the polymers contain a free carboxylic acid group on the carboxyl end of the polymer chain; "M" indicates an ester end group.

TABLE 2

Specifications of Medisorb ® Biodegradable Polymers

| Medisorb Polymer | Inherent Viscosity (dL/g) | Approx. MW (Kd) | DL-lactide/glycolide mole ratio |
|---|---|---|---|
| 5050DL2A | 0.15 | 12.3 | 53/47 |
| 5050DL2M | 0.18 | 17.3 | 54/46 |
| 5050DL3A | 0.25-0.33 | 20-28 | 54/46 |

Other materials utilized include insulin, cytochrome-C, tetanus and diphtheria toxoids, ethyl alcohol (USP grade), distilled water, and polyvinyl alcohol (PVA).

Example 1

SCCNC Polymer Microspheres/Nanospheres Formed with Near-Critical Propane

Polymer microspheres/nanospheres were formed with 50:50 PLGA obtained from Sigma Chemicals (St. Louis, Mo.) in the SCCNC polymer sphere apparatus running in the continuous mode. The polymer microspheres/nanospheres were formed by injecting the SCCNC polymer solution into distilled water. The resulting product was observed under a light microscope, and the particle sizes were measured in a Coulter 4MD sub-micron particle size analyzer. The volume of distilled water used in PMF-03a was about half of that used in PMF-01 resulting in a more concentrated microsphere solution and a different particle size distribution. Some of these results are presented in Table 3.

TABLE 3

SCCNC Polymer Microspheres/Nanospheres Formed with 50:50 PLGA at 40° C.

| Run No. | SCCNC | Pressure (psig) | Flow Rate (mL/min) | Small Size (nm)/% | Medium Size (nm)/% | Large Size (nm)/% |
|---|---|---|---|---|---|---|
| PMF-01 | $C_3H_8$ | 2,000 | 1.0 | 99 (26%) | 336 (74%) | |
| PMF-02a | $C_3H_8$ | 4,000 | 1.0 | | 120 (34%) | 2,120 (66%) |
| PMF-02b | $C_3H_8$ | 5,000 | 3.0 | 33 (57%) | 282 (15%) | 10,000 (29%) |
| PMF-03a | $C_3H_8$ | 2,000 | 1.0 | | 291 (76%) | 1,770 (24%) |
| PMF-03b | $C_3H_8$ | 2,000 | 4.0 | | 169 (33%) | 852 (67%) |

Example 2

Protein Antigenicity in Polymer Microspheres Formed by Different SCCNC

Experiments were performed to encapsulate tetanus toxoid (TT) and diphtheria toxoid (DT) vaccine antigens in 50:50 PLGA polymer microspheres formed by SCCNC carbon dioxide and propane. In these tests, DT and TT were each separately treated with supercritical carbon dioxide with 10% (v/v) cosolvent ethanol, and near-critical propane in the presence of PLGA. The pressure and temperature were around 3,000 psig and 30-35° C. respectively. The protein and antigenicity activities were performed by micro BCA assay and a sandwich-type capture ELISA [Gupta, R. K., Siber, G. R., Alonso, M. J. and Langer, R., in *Modern Approaches To New Vaccines Including Prevention of AIDS*. Ed. by Ginsberg, H. S., Brown, F., Chanock, R. M. and Lerner, R. A. Cold Spring Harbor Laboratory, Press, 1993] assay. The results of this study are summarized in Table 4.

TABLE 4

Protein Content and Antigenicity of Tetanus Toxoid and Diphtheria Toxoid in PLGA Polymer Microspheres formed by Different SCCNC

| Sample No. | Toxoid | SCCNC | Protein (mg/mL) | ELISA (Lf/mL) |
|---|---|---|---|---|
| 1 | Diphtheria | Control | 21.07 | 7.35 |
| 2 | Diphtheria | $CO_2$/ethanol | 1.49 | 0.13 |
| 3 | Diphtheria | $C_3H_8$ | 18.63 | 6.55 |
| 4 | Tetanus | Control | 30.44 | 9.0 |
| 5 | Tetanus | $CO_2$/ethanol | 9.81 | 0.44 |

Both diphtheria and tetanus toxoids lost most of their antigenicity after being treated with SCCNC carbon dioxide/ethanol mixtures. These losses are probably due to the fact that the acid/base equilibrium shifted due to the formation of carbonic acid when the aqueous protein is exposed to carbon dioxide. This shift can drastically reduce pH if the solution is insufficiently buffered. Both diphtheria and tetanus toxoids will denature at pH levels below 5.0. Thus, carbon dioxide may not be the best candidate for a SCCNC solvent for acid pH sensitive proteins. Propane, on the other hand, did little damage to the diphtheria toxoid because it has negligible impact on the acid/base equilibrium of the aqueous protein.

Example 3

Protein (Insulin) Encapsulation by SCCNC Polymer Microspheres/Nanospheres

Experiments were conducted to encapsulate insulin in polymer microspheres/nanospheres utilizing supercritical carbon dioxide. Insulin, which has an isoelectric point of 3.65, is stable at acid pHs. In these experiments, a feed solution of 0.1 mg/mL insulin in 90% ethanol:10% water was utilized. The supercritical carbon dioxide was pumped at a rate of 1 mL/min, the cosolvent pump at 0.1 mL/min, and the insulin solution at 0.5 mL/min. The resultant mixture was injected into 8 mL of 1% PVA solution for 30 minutes. The results of these experiments are summarized in Table 5.

TABLE 5

Polymer Microspheres/Nanospheres Formed with Medisorb Polymers and Insulin in SCCNC Carbon Dioxide/Cosolvent at 3,000 psig and 50° C.

| Run No. | Polymer | SCCNC | Small Size (nm) | Medium Size (nm) | Large Size (nm)/% |
|---|---|---|---|---|---|
| MS-09 | DL2A | $CO_2$/ethanol | | 750 (22%) | 5,250 (77%) |
| MS-10 | DL2M | $CO_2$/ethanol | | 634 (100%) | |
| MS-11 | DL3A | $CO_2$/ethanol | | 300 (49%) | 10,000 (51%) |
| MS-12 | DL2A | $CO_2$/acetone | | 326 (100%) | |

The data in Table 5 indicates that the Medisorb DL2M and DL2A bioadhesive polymers formed relatively uniform particle size distributions in the SCCNC $CO_2$/ethanol and SCCNC $CO_2$/acetone systems, respectively, at 3,000 psig and 50° C.

Example 4

Release of Cytochrome-C from SCCNC Polymer Microspheres/Nanospheres

In order to establish conditions for the encapsulation of proteins in uniform microspheres and their release characteristics, several experiments were conducted to encapsulate cytochrome-C in polymer microspheres/nanospheres utilizing supercritical carbon dioxide. In these experiments, a feed solution of 0.1 mg/mL cytochrome-C in 99% ethanol:1% water was utilized. The supercritical carbon dioxide was pumped at a rate of 1.0 mL/min, the cosolvent pump at 0.1 mL/min, and the cytochrome-C solution at 0.5 mL/min. The resultant mixture was injected into 8 mL of 1% PVA solution for 30 minutes. The results of some of these experiments are summarized in Table 6.

TABLE 6

Polymer Microspheres/Nanospheres Formed with Medisorb Polymers and Cytochrome-C in SCCNC Carbon Dioxide and Propane at 3,000 psig

| Run No. | Polymer | SCCNC | Temp. (° C.) | Small Size (nm) | Medium Size (nm) | Large Size (nm) |
|---|---|---|---|---|---|---|
| MS-19 | DL3A | $CO_2$/10% ethanol | 45 | | 318 (100%) | |
| MS-21 | DL2A | $CO_2$/10% ethanol | 45 | | 292 (100%) | |
| MS-22 | DL2A | $CO_2$/10% acetone | 45 | | 267 (100%) | |
| MS-23 | DL2M | $CO_2$/10% ethanol | 45 | | 239 (100%) | |
| MS-24 | DL2A | $C_3H_8$/10% acetone | 30 | | 187 (100%) | |
| MS-25 | DL2A | $C_3H_8$/3% acetone | 40 | | 418 (100%) | |

Some of the size distributions were quite narrow while others were broad. Some of the charts indicate the presence of "dust" which are particles that are larger than 10 micron in size. Most of these particles, from microscopic observations, appear to be excess polymer. These large polymer particles were removed by vacuum filtration prior to solvent evaporation and drying to harden the polymer microspheres/nanospheres. In experiments MS-24 and MS-25, the supercritical fluid and cosolvent pumps were kept in operation for 180 minutes after the feed pump was turned off to ensure that all the protein had been displaced from the high pressure circulation loop.

Figure 2:
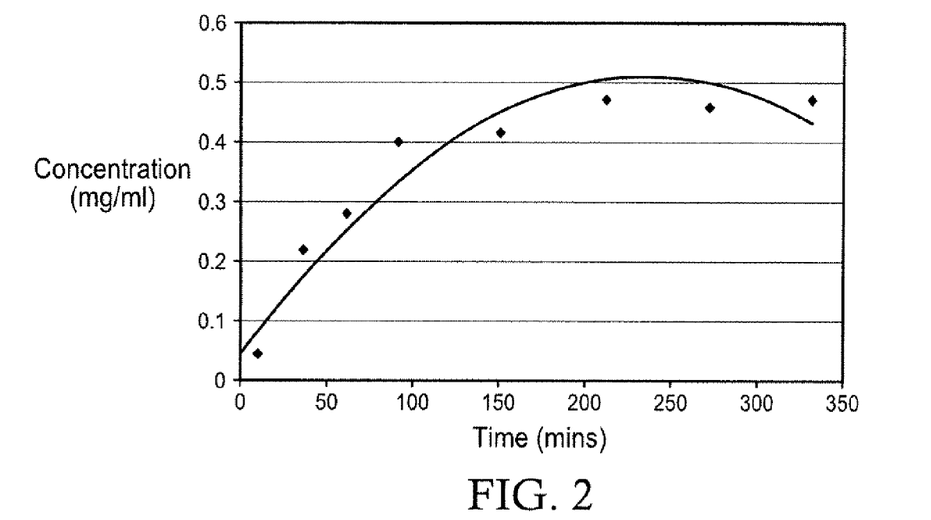
FIG. 2 is a graph of the in vitro time release characteristics of cytochrome-C from SCCNC polymer spheres.

The release characteristics of MS-25 were evaluated by suspending the dried microspheres in 4 mL of PBS at a pH of 7.4. Absorption of the solution was then measured at 408 nm and over the 350 to 450 nm range at different time intervals. Concentration was determined from a standard curve. The release characteristics of MS-25 over a 5 hour period is shown in FIG. 2.

Example 5

In Vitro Release of Insulin from SCCNC Polymer Microspheres/Nanospheres

Figure 3:
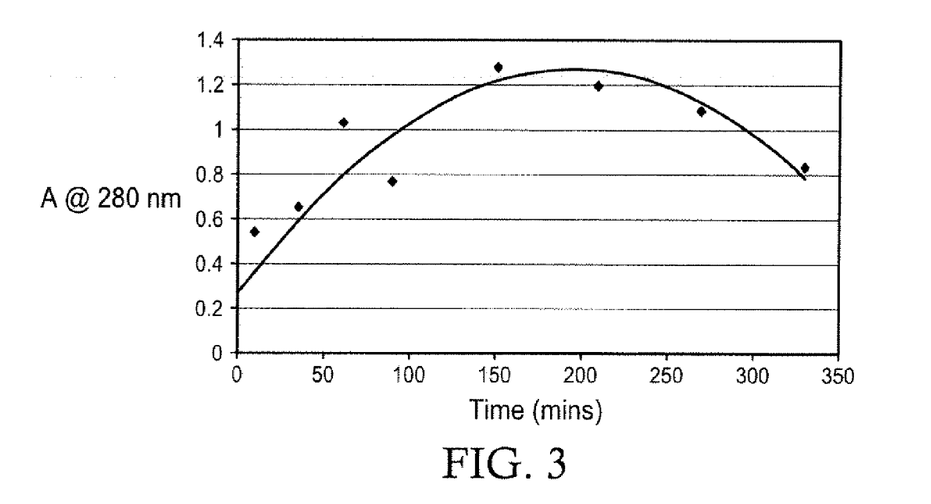
FIG. 3 is a graph of the in vitro time release characteristics of insulin from SCCNC polymer nanospheres.

In this example, a feed solution of 0.1 mg/mL insulin in 90% ethanol:10% water was utilized. Supercritical carbon dioxide was pumped at a rate of 1.0 mL/min, the cosolvent pump at 0.1 mL/min, and the insulin solution at 0.5 mL/min. The resultant mixture was injected into 8 mL of 1% PVA solution for 30 minutes. The supercritical fluid and cosolvent pumps were kept in operation for 180 minutes after the feed pump was turned off to ensure that all the protein had been displaced from the high pressure circulation loop. The release characteristics of insulin in this experiment MS-27 was evaluated by suspending the dried microspheres in 4 mL of PBS at a pH of 7.4. Absorption of the solution was then measured at 280 nm and over the 250 to 350 nm range at different time intervals. The release characteristics of MS-27 over a 5-hour period are shown in FIG. 3.

Example 6

In Vivo Release of Insulin from SCCNC Polymer Microspheres/Nanospheres

A preliminary study with SCCNC polymer nanoencapsulated insulin was conducted in diabetic rats. Three groups of four chronic diabetic BB/Wor male rats were used to evaluate efficacy on nanoencapsulated insulin (MS-29). One group [A] was given 2 ml of the test formulation (MS-29) using the standard gavage method. The second group [B] received oral non-encapsulated insulin, administered by gavage at the concentration based on the animals' day of diabetes onset. A third group [C] received injected insulin (PZI, Eli Lilly) therapy at the dose consistent with their day of onset of diabetes. The animals were bled prior to treatment and at 0.5, 1, 2, 4, 8, and 16 hrs after treatment. The results are summarized in Table 7.

TABLE 7

Percent Change in Glucose Concentration in Diabetic Rats (mg/dL)

| Post-Treatment Time | A Test Article (MS-29) | B Oral Insulin | C Injected Insulin |
|---|---|---|---|
| 0.5 hr | −22.1% | +2.9% | −47.4% |
| 1 hr | −22.8% | −4.6% | −62.7% |
| 2 hr | −22.1% | −24.4% | −71.8% |
| 4 hr | +17.6% | +2.8% | −37.9% |
| 8 hr | +13.5% | +7.5% | −48.5% |
| 16 hr | +35.4% | +47.3% | −37.6% |

The results of this in vivo study [Column A] showed a significant decrease in glucose levels at 0.5, 1 and 2 hours after the oral administration of SCCNC polymer nanoencapsulated insulin. While the duration was only for 2 hours, it was immediate and consistent. The duration can be improved by increasing dosage levels and/or polymer molecular weight/type that will determine the integrity of the SCCNC polymer nanospheres.

Non-encapsulated insulin given orally by gavage only showed a statistical decrease in the level of glucose at one time point, 2 hours [Column B]. At all other times, oral insulin did not statistically decrease the levels of glucose in diabetic rats.

The positive control, injected insulin in Column C, caused a statistical decrease in glucose levels at all times measured post treatment.

Example 7

SuperFluids Microsphere/Nanosphere Apparatus with Integral Solubility Unit

A SuperFluids Microsphere/Nanosphere Apparatus with Integral Solubility Unit 61 is shown in FIG. 4. This apparatus consists of a mixing chamber 63, a solids chamber 65 for containing the polymer, a high pressure circulation pump 67, a multi-port Valco sampling valve 69, a static in-line mixer 71, two back pressure regulators (BPR) 73 and 75, two injectors or nozzles 77 and 79 and two sample collection chambers 81 and 83 all contained in a temperature controlled chamber 85. External to this chamber, three syringe pumps 87, 89 and 91 (Isco, Inc., Lincoln, Nebr.), are respectively used for delivery of the supercritical fluid, cosolvent and protein therapeutics.

The mixing chamber 63, solids chamber 65, circulation pump 67 and sampling valve 69 are connected in a high-pressure circulation loop with a total volume of approximately 160 ml. The fluids exiting the supercritical fluid syringe pump outlet 93 and cosolvent syringe pump outlet 95 are intermixed at a mixing tee 97 and fed into the high-pressure circulation loop at the entrance of the solids chamber 65. There are two take-offs from the high-pressure circulation loop. The first take-off can be achieved by switching the sample valve 69 to allow the circulating stream to flow through a 500 microliters sampling loop 99. After the sample is trapped, the sampling loop is flushed with a liquid solvent from the flush solvent injector 101 such as acetone to collect the polymer dissolved in 500 microliters of SuperFluid™ in a solubility sample collection vessel 103. The second take-off from the high-pressure circulation loop is at the top of the mixing chamber 63. This take-off is connected to the inlet 105 of a static in-line mixer 71. The feed syringe pump 91 for a protein rich stream is also connected to the inlet 105 of the static in-line mixer 71. The system is maintained as a closed system. The entire apparatus up to the back-pressure regulators 73 and 75 is designed to operate up to 5,000 psig and 60° C. The apparatus is cleaned in-place by washing with a series of solvents including bleach, caustic and dilute hydrochloric acid, and then sterilized in-place with an ethanol/water (70/30) mixture.

Biodegradable Polymers: Polymer encapsulation experiments were conducted with various biodegradable poly(D,L-lactic glycolic acid) since the size and integrity of the polymer microspheres depends on the polymer type and size. Examples of biodegradable polymers that can be used in the invention include, but are not limited to, Medisorb® biodegradable PLGA poly(D,L-lactic glycolic acid) polymers (Alkermes, Inc., Cincinnati, Ohio)—5050DL2A with an inherent viscosity of 0.15 dL/g and an average MW of 12.3 KD; 5050DL2M with an inherent viscosity of 0.18 dL/g and an average MW of 17.3 KD; and 5050DL3A with an inherent viscosity range of 0.25 to 0.33 dL/g and a MW range of 20 to 28 KD. "A" indicates that the polymers contain a free carboxylic acid group on the carboxyl end of the polymer chain; "M" indicates an ester end group. Another example is Resomer® RG 502 PLGA (Boehringer Ingelheim KG) with an inherent viscosity of 0.16-0.24 dL/g and glass transition temperature range of 40-55° C.

SuperFluids™ Polymer Solubility Optimization: Our results and theoretical considerations indicate that the optimal formation of polymer microspheres and encapsulation of betulinic acid depends on polymer SuperFluids™ solubility, nozzle size and type, rate of bubble formation, characteristics of the micro/nanoparticle forming media including cosolvent type and concentration and polymer/betulinic acid ratios. Conditions for optimum polymer solubilization in a SuperFluids™ stream depend on several parameters including the composition and molecular weight of the bioadhesive polymer, SuperFluids™ type, pressure and temperature, and cosolvent type and concentration. The physical properties of supercritical fluids that affect solubility of polymers are shown in Table 8. Physical properties of some other critical fluid solvents are shown in Table 1.

TABLE 8

Physical Properties of Selected Supercritical Fluid Solvents

| SuperFluids ™ | Formula | BP (° C.) | $P_{vap}$ (psia @ 25° C.) | $T_c$ (° C.) | $P_c$ (psia) | Dipole Moment (debyes) |
|---|---|---|---|---|---|---|
| Carbon dioxide | $CO_2$ | −78.5 | 860 | 31.1 | 1070 | 0.0 |
| Nitrous oxide | $N_2O$ | −88.5 | 700 | 36.5 | 1051 | 0.2 |
| Freon 23 | $CHF_3$ | −82.2 | 630 | 26.1 | 700 | 1.6 |

BP = Normal boiling point;
$P_{vap}$ = Vapor pressure;
$T_c$ = Critical Temperature;
$P_c$ = Critical Pressure Carbon dioxide has a critical temperature that is near-ambient, is very nonpolar having a dipole moment of 0.0 Debyes and behaves very much like hexane in the supercritical fluid and near-critical fluid regime. This most popular supercritical fluid is nontoxic, inexpensive and almost environmentally benign. The primary disadvantage of carbon dioxide is that it forms carbonic acid in an aqueous solution that may be harmful to most proteins. This disadvantage will not impact proteins with low isoelectric points. Nitrous oxide is about the same molecular size as carbon dioxide and has similar critical properties. However, nitrous oxide is slightly polar having a dipole moment of 0.2 Debyes. Nitrous oxide should thus be a more favorable solvent for bioadhesive polymers, and would minimize the use of co-solvents. Freon-23, trifluoromethane, is an excellent candidate since it is not chlorinated (ozone depletion is thought to be caused by chlorine in the atmosphere) and has a much lower critical temperature than Freon-22 (see Table 1). For large-scale manufacturing, the SFS will be recycled in order to minimize costs.

Pressure and temperature both impact density or solvation capacity and solubility parameter or selectivity. Adequate solubilities should fall within a pressure range of 1000-5000 psig since density often reaches an asymptote at reduced temperatures approaching 3.0, e.g. approximately 3,000 psig for carbon dioxide and nitrous oxide. Temperatures over the range of 10° C. to 60° C. will provide sufficient solubility, especially those temperatures above the phase transition temperatures of biodegradable polymers. The density and solubility parameters of SuperFluids™ are inversely related to pressure and temperature, i.e. they increase with a decrease in temperature and an increase in pressure. For example, the 
solubility parameters of nitrous oxide at 4,000 psig and 40° C., 2,000 psig and 22° C. and 1,000 psig and 10° C. are approximately the same.

Acetone and ethanol can be utilized over a concentration range of 0 to 20%, on the solubility of selected polymers in the different SuperFluids™. Polar modifiers or cosolvents such as acetone and ethanol form a single miscible phase with most SCCNC over the range of temperature, pressure and cosolvent concentrations used. Miscibility can be confirmed from published phase diagrams and/or direct experiments in a high-pressure sight-glass. Polar modifiers effectively modify the polarity of nonpolar SCCNC and their selectivities for differing polarity molecules, e.g. carbon dioxide with 20% ethanol has a solubility parameter identical to that of Freon-23 at certain conditions of temperature and pressure.

SuperFluids™ Polymer Microspheres Encapsulation Optimization: Polymer will come out of solution after decompression and form a thin film on the inside of a bubble formed by the SFS exiting the injection nozzle. The size of this bubble depends on the size of the injection nozzle as well as other parameters such as flowrate. The bubble disengages from the nozzle tip and "pops" as a result of gas expansion and hydrodynamic forces. The bubble should break into uniform parts, the size of which will depend on the size of the bubble that in turn depends on the size of the nozzle, forming uniform particles. The size of the polymer particle thus depends on the size of the nozzle.

Depending upon the type of polymer and operational conditions, we have shown that a narrow size distribution of nanospheres, around 200 to 400 nanometers can be obtained by the SuperFluids™ process with a 10 mil (internal diameter of 0.25 mm or 250 micron) capillary injection nozzle. Larger internal diameter 316 stainless steel capillary tubes can be utilized to increase polymer particle size. Impingement nozzles (Bete Fog Nozzle, Inc., Greenfield, Mass.) can also be utilized. Nozzle impingement may prevent the coagulation of polymeric particles resulting from high concentrations of polymer particles formed under rapid flow conditions.

The characteristics of the medium in which the polymer microspheres are formed impacts their size, uniformity and stability. Polymer microspheres were formed by injecting the polymer-rich SuperFluids™ and particle-rich streams into a 1% polyvinyl alcohol (PVA) solution, primarily to prevent particle agglomeration. The concentration of PVA can be varied to determine its impact on particle size and uniformity. The use of other media, such as high concentration sucrose solutions, may aid in particle stability during lyophilization. Liquid nitrogen can be used for freezing the particles.

Other collection media parameters that could impact the size and uniformity of the microspheres/nanospheres are temperature and pressure. Lower temperatures should be much more favorable for polymer particle stabilities. There may be some benefits for temperatures above the phase transition temperature. Pressure in the particle formation chamber will help control the size and uniformity of bubbles formed and microspheres/nanospheres generated. The pressure in the particle formation chamber can be varied from the vapor pressure of the neat SCCNC at the temperature of the medium to atmospheric pressure.

Optimum polymer microsphere/nanosphere formation, size and betulinic acid encapsulation depends on the ratio of polymer to protein in the sample collection chamber(s). This ratio depends on the flowrate of the protein-rich stream and its concentration, and the flowrate of the polymer-rich SuperFluids™ stream and its concentration (which is defined by polymer solubility at operating conditions). Polymer: protein ratios can be from 100:1 to 1:1, preferably 10:1.

Example 8

Solubility of Polyethylene Glycol 3350 in Superfluids™

The solubility of Polyethylene Glycol (PEG) in SuperFluids™ was measured in order to establish conditions for utilizing SuperFluids™ to preferentially extract/remove PEG from hydrophilic microspheres containing therapeutic proteins.

PEG, $H(OCH_2CH_2)_nOH$ [CAS No. 2532-68-3], is a waxy solid having an average Molecular Weight of 3,373 (3,015-3,685), a density of 1.0926 g/ml at 20° C. and a melting point range of 54-58° C.

In this first series of solubility experiments, thirteen (13) experiments were conducted on PEG [Spectrum Chemicals & Laboratory Products, New Brunswick, N.J.]. The first three experiments were conducted to obtain the best loading conditions in the PEG sample chamber. In the subsequent ten (10) experiments, glass wool and approximately 200 to 300 mg of PEG 3350 were layered inside a 10 ml 316-SS extraction chamber that was then placed in the temperature controlled SFX-210 unit. Both sample and glass wool were removed from the extraction chamber after each run, weighed and extracted for mass balance purposes. A fresh set of glass wool and sample material was used in each run.

During each run, the high-pressure loop was sampled five times [5, 15, 30, 45 and 60 minutes] with a 5.0 ml loop. The contents of the sample loop were vented into ethanol into a pre-weighed glass vial; the sample loop was then flushed with water followed by methanol and acetone into the same glass vial in order to remove any residual materials that may have been deposited in the sample loop during the venting process. The solvents collected from the vent and flush steps were dried in a SpeedVac at low to moderate temperatures for several hours. The glass vials were then weighed to determine the amount of PEG 3350 that was dissolved in the 5 ml sample loop.

Two of the most consistent data points were averaged to provide the results listed in Table 9. In some of the higher solubility runs, the amount dissolved in the 5 ml sample loop decreased after the $1^{st}$ sample, presumably from the reduced availability of PEG 3350 in the high-pressure circulation loop. In such cases, an average was taken of the first two measurements; this average could thus be conservatively lower that the actual solubility.

TABLE 9

Solubility of PEG 3350 in Different SuperFluids ™ Solvents

| Run No. | Fluid | Cosolvent | Ratio [vol %] | Temp. [C.] | Press. [psig] | Density [g/ml] | Solubility [w/w, %] | Solubility [mg/ml] |
|---|---|---|---|---|---|---|---|---|
| PEGS-4 | CO2 | None | 100:0 | 40 | 2,500 | 0.819 | 0.000 | 0.00 |
| PEGS-5 | CO2 | Ethanol | 90:10 | 40 | 2,500 | 0.816 | 0.004 | 0.03 |

TABLE 9-continued Solubility of PEG 3350 in Different SuperFluids ™ Solvents

| Run No. | Fluid | Cosolvent | Ratio [vol %] | Temp. [C.] | Press. [psig] | Density [g/ml] | Solubility [w/w, %] | Solubility [mg/ml] |
|---|---|---|---|---|---|---|---|---|
| PEGS-6 | CO2 | Ethanol | 80:20 | 40 | 2,500 | 0.813 | 0.037 | 0.30 |
| PEGS-7 | CO2 | Ethanol | 70:30 | 40 | 2,500 | 0.810 | 1.316 | 10.66 |
| PEGS-8 | CO2 | Ethanol | 60:40 | 40 | 2,500 | 0.807 | 1.511 | 12.20 |
| PEGS-9 | CO2 | Ethanol | 50:50 | 40 | 2,500 | 0.805 | 1.548 | 12.45 |
| PEGS-10 | CO2 | Ethanol | 70:30 | 40 | 1,000 | 0.374 | 2.455 | 9.17 |
| PEGS-11 | CO2 | Ethanol | 70:30 | 40 | 5,000 | 0.895 | 1.342 | 12.01 |
| PEGS-12 | CO2 | Ethanol | 70:30 | 20 | 2,500 | 0.889 | 1.588 | 14.12 |
| PEGS-13 | CO2 | Ethanol | 70:30 | 30 | 2,500 | 0.854 | 1.342 | 11.47 |

Figure 7:
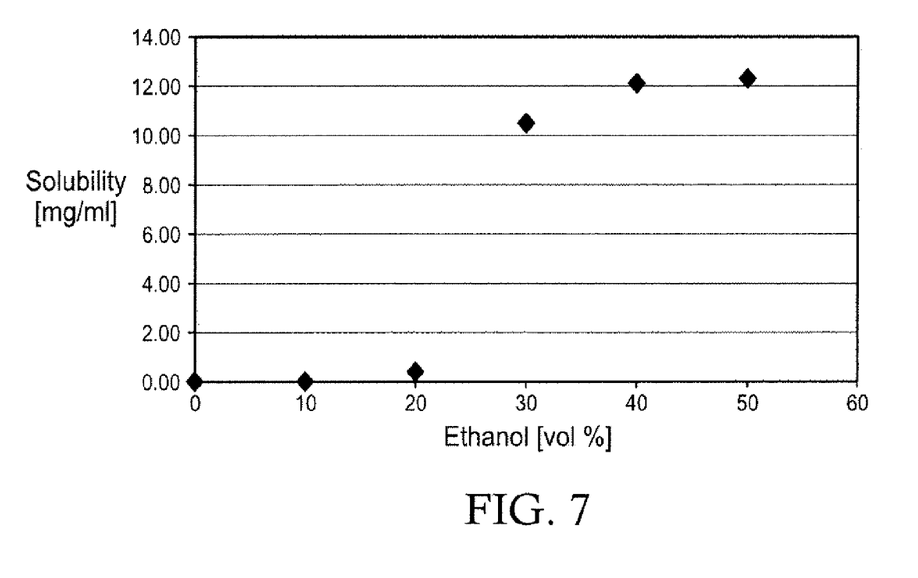
FIG. 7 is a graph of the solubility of PEG in CO2:Ethanol at 40° C. and 2,500 psig as a Function of Ethanol Concentration [vol %]

The data in FIG. 7 shows a sigmoidal increase in solubility with increase in ethanol concentration, plateauing out at about 40 to 50% ethanol. Perturbations were made around the 70:30::CO2:ethanol mixture in an effort to maximize solubility while minimizing ethanol concentration.

Figure 8:
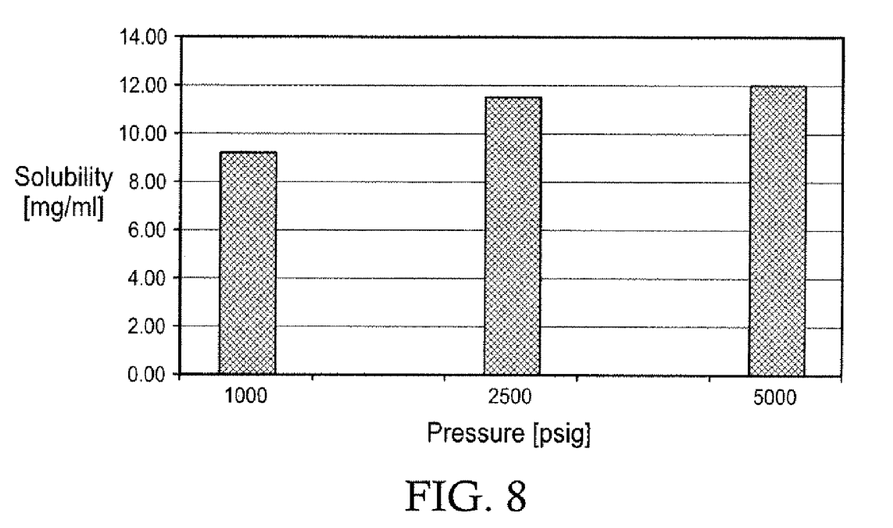
FIG. 8 is a bar graph of the solubility of PEG in CO2:Ethanol::70:30 at 40° C. as a Function of Pressure.

The data in FIG. 8 indicates that the solubility of PEG 3350 in $CO_2$:Ethanol::70:30 at 40° C. increases with pressure and appears to flatten out between 2,500 and 5,000 psig.

Figure 9:
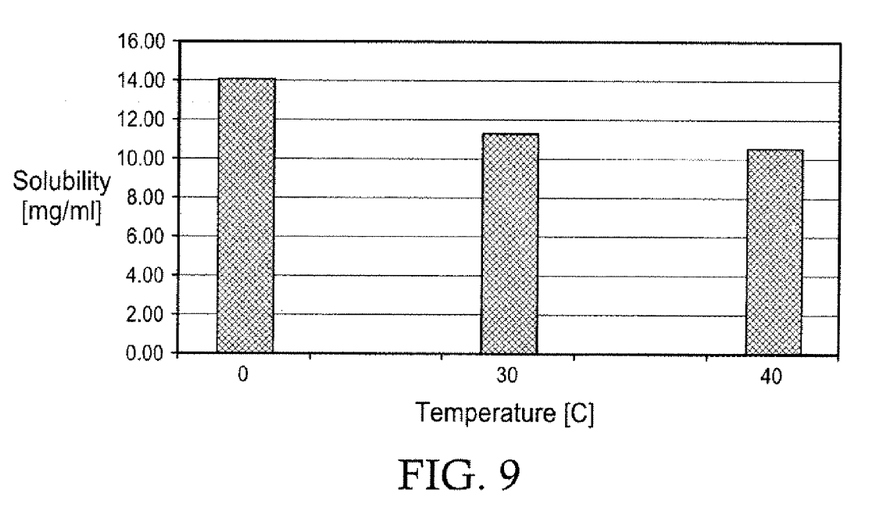
FIG. 9 is a bar graph of the solubility of PEG 3350 in CO2:Ethanol::70:30 at 2,500 psig as a Function of Temperature.

The data in FIG. 9 indicates that the solubility of PEG 3350 in $CO_2$:Ethanol::70:30 at 2,500 psig decreases with increased temperature and appears to flatten out between 30 and 40° C.

The data and graphs suggest the best SuperFluids™ conditions for the solvation of PEG 3350 are a 70:30 mixture of $CO_2$:ethanol at 2,500 psig and 20° C., having a solubility of 1.59 w/w % and 14.12 mg/ml.

SuperFluids™ $CO_2$:ethanol may find utility in the selective removal of PEG 3350 from hydrophilic microspheres containing therapeutic proteins. Carbon dioxide—with a very modest critical point (31° C. and 1,070 psia)—is inexpensive, non-toxic, non-flammable and, for the most part, environmentally acceptable. Supercritical carbon dioxide has a density of 0.74 gm/ml at a pressure of 2,000 psia and a temperature of 40° C. Around these conditions, $CO_2$ behaves like an organic solvent (hexane) with solubilization characteristics of a liquid and the permeabilization characteristics of a gas. Carbon dioxide, however, may negatively impact the integrity of the therapeutic protein through acid hydrolysis. Ethanol may also negatively impact the nature of the proteins. These fluids combined in the proposed ratios are fully miscible and behave like a unique, independent solvent. Thus, the impact of SuperFluids™ $CO_2$:ethanol on therapeutic proteins is not totally predictable.

Based on the experimental data and molecular thermodynamics, the solubility of PEG 3350 can be optimized for SuperFluids™ such as Propane, Freon-23 and Freon-22. It may be quite possible to utilize these without cosolvents such as ethanol or at least a minimum of cosolvent. Near-critical propane is only very slightly polar, having a dipole moment of 0.084 debyes—a factor which may also contribute to its solvation selectivity in the presence of appropriate cosolvents. Since propane is a flammable solvent, even though it is GRAS by the FDA, the use of fluorinated propane is recommended for reasons of safety. Freon-23, trifluoromethane (CHF3, 1,1-dichloro-2,2,2-trifluoro-ethane, referred to as HCFC-123) is a non-chlorinated fluorocarbon with a critical temperature of 25.9° C., a critical pressure of 686.5 psia and a dipole moment of 1.6 Debyes. Freon-23 is a very interesting solvent because it has a large dipole moment, is potentially polarizable because of its hydrogen content, and does not contribute to ozone depletion because of the lack of a chlorine atom.

It is intended that the matter contained in the preceding description be interpreted in an illustrative rather than a limiting sense. Although the invention has been described with respect to various embodiments, this invention also encompasses a wide variety of further and other embodiments within the scope and spirit of the teachings herein.

What is claimed is:

1. A method of purifying protein-containing-polymer-microspheres comprising
    loading a PEG protein-containing-polymer-microspheres product into a column extractor;
    pressurizing the extractor with a supercritical or near-critical fluid;
    charging a first pump with a supercritical or near-critical fluid;
    charging a second pump with a cosolvent;
    pressurizing the pumps;
    mixing the supercritical or near-critical fluid with the cosolvent under pressure;
    flowing the fluid-cosolvent mixture through the extractor;
    collecting PEG solubilized in cosolvent;
    decompressing the extractor; and
    recovering purified protein-containing-polymer-microspheres.

2. The method of claim 1, wherein said supercritical or near-critical fluid is selected from the group consisting of carbon dioxide, propane, fluorinated propane, Freon-23 and Freon 22.

3. The method of claim 1, wherein said cosolvent is ethanol or methanol.

4. The method of claim 1, wherein said fluid-cosolvent mixture comprises carbon dioxide:ethanol::70:30.

5. The method of claim 1, wherein said pressure is about 2500 psig-5000 psig.

6. The method of claim 1, wherein the temperature is about 10° C.-40° C.

* * * * *